United States Patent [19]

Utting et al.

[11] Patent Number: 4,481,209

[45] Date of Patent: Nov. 6, 1984

[54] PENICILLIN SALT

[75] Inventors: Kenneth Utting, Lower Kingswood; Karrar A. Khan; Sidney E. Callander, both of Worthing, all of England

[73] Assignee: Beecham Group Limited, England

[21] Appl. No.: 204,845

[22] Filed: Nov. 7, 1980

Related U.S. Application Data

[63] Continuation of Ser. No. 25,662, Mar. 30, 1979, abandoned.

[30] Foreign Application Priority Data

Apr. 1, 1978 [GB] United Kingdom ............... 12823/78

[51] Int. Cl.$^3$ ..................... A61K 31/43; C07D 499/32
[52] U.S. Cl. ................................. 424/271; 260/239.1
[58] Field of Search ...................... 260/239.1; 424/271

[56] References Cited

U.S. PATENT DOCUMENTS

| 3,180,862 | 4/1965 | Silvestri et al. | 260/239.1 |
| 3,534,035 | 10/1970 | Nescio | 260/239.1 |
| 3,674,776 | 7/1972 | Long et al. | 260/239.1 |
| 3,860,579 | 1/1975 | Ferres et al. | 260/239.1 |

Primary Examiner—Natalie Trousof
Assistant Examiner—Vera C. Clarke
Attorney, Agent, or Firm—Jacobs & Jacobs

[57] ABSTRACT

Ampicillin phthalidyl ester naphthalene-2-sulphonate, its preparation, and its use in pharmaceutical compositions to treat infections.

8 Claims, No Drawings

PENICILLIN SALT

CROSS-REFERENCE

This is a continuation of Ser. No. 025,667 filed Mar. 30, 1979, now abandoned.

This invention relates to a penicillin salt. More specifically this invention relates to the naphthalene 2-suphonate salt of ampicillin phthalidyl ester, its preparation, and its use in the therapy of disease.

U.K. Pat. No. 1,364,672 described and claims the phthalidyl ester of 6-[D(−)-α-aminophenylacetamido]-penicillanic acid, of formula (I):

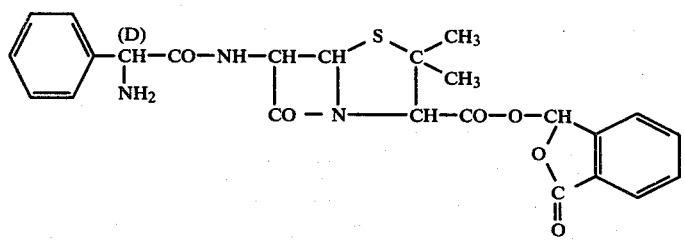

and pharmaceutically acceptable acid addition salts thereof. This penicillin, hereinafter referred to as talampicillin, and its acid addition salts produce high serum concentrations of the parent penicillin, ampicillin, when administered orally.

Due to its ready solubility and ease of preparation, talampicillin is normally used in the form of its hydrochloride salt. However, in this form the ester has an unpleasant taste which makes formulations thereof such as syrups and uncoated tablets unpalatable.

It is an object of this invention to provide a form of talampicillin which has a greatly improved taste relative to talampicillin hydrochloride whilst retaining therapeutically effective bioavailability.

The object has been achieved by the provision of ampicillin phthalidyl ester naphthalene 2-sulphonate. It should be noted that U.K. Pat. No. 1,364,672 discloses that talampicillin can form salts with inorganic and organic acids (especially those which have been employed to form salts with ampicillin). However in this U.K. Patent the only salt specifically exemplified is the hydrochloride salt, and there is no suggestion that the specific salt of this invention should be prepared or that very advantageous properties could be obtained therewith.

Accordingly, the present invention provides ampicillin phthalidyl ester naphthalene 2-sulphonate.

Ampicillin phthalidyl ester naphthalene 2-sulphonate, hereinafter referred to as talampicillin napsylate, has the structure (A):

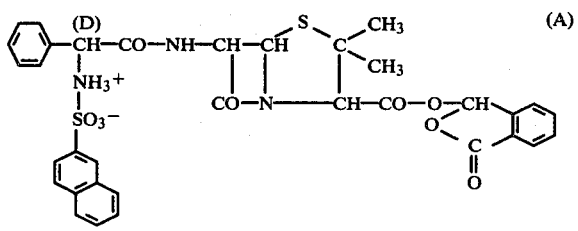

The invention also provides a process for the preparation of talampicillin napsylate, which process comprises reacting together a source of ampicillin, a source of napsylate ions and a source of the 3-phthalidyl group.

It will be appreciated that talampicillin will conveniently act as both a source of ampicillin and a source of the phthalidyl group.

Thus one preferred process of the reaction comprises contacting talampicillin, or a salt thereof, with naphthalene 2-sulphonic acid, or a salt thereof.

Normally this reaction is carried out in an aqueous solvent, such as water or an aqueous organic solvent mixture such as aqueous methylene dichloride. In such cases the talampicillin is used in the form of a water soluble salt, such as the hydrochloride salt. Similarly, in such cases the naphthalene 2-sulphonic acid is used in the form of a water soluble salt, such as the sodium salt.

The product of the reaction can be isolated in any suitable manner. Suitable methods include precipitation from an essentially water solvent, followed by filtration; dissolution of a precipitated product in an organic solvent, such as methylene dichloride, and then spray drying this solution; and carrying out the process in an aqueous organic solvent mixture, isolating the organic phase after the reaction is complete, and then spray drying this organic phase.

In one such preferred reaction system, a solution in water of sodium naphthalene-2-sulphonate is added to a solution in water of talampicillin hydrochloride. In such cases we have found that the concentration of the talampicillin hydrochloride solution can be increased (at a given reaction temperature) if a gel inhibitor is included in the solution.

Suitable gel inhibitors for this use include secondary butanol (for example at 3% v/v); urea (for example at 6% w/v); acetic acid (for example at 1% v/v); polyvinylpyrrolidone, suitably of molecular weight 2000–3500 or 10,000 (for example at 10% w/v); polyethylene glycol, suitably of molecular weight 600 (for example at 10% v/v); and ethylene glycol (for example at 10% v/v).

By way of example we have found that suitable concentrations of talampicillin hydrochloride solutions for use in the reaction can be increased from about 4 to 5% at 20° to 25° C. to about 7.5 to 10% at the same temperature using a gel inhibitor as described.

In a further useful process modification the talampicillin hydrochloride for reaction with the naphthalene-2-sulphonic acid salt can be produced by means of phase transfer catalysis, in the manner described in West German Offenlegungsschrift No. 2656062.3 or U.S. Pat. No. 4,072,677. In this way isolation of the talampicillin hydrochloride can be avoided.

It will also be appreciated that talampicillin having its amino group protected with an acid-sensitive protecting group can act as the source of ampicillin and phthalidyl group in the process of the invention. In such cases, of course, acid hydrolysis of the N-protecting group, for example an enamine group, will generate the corresponding talampicillin acid addition salt, and then this salt can be reacted in the usual way with a source of napsylate ions. Alternatively however the N-protected talampicillin can be reacted with naphthalene 2-sulphonic acid to effect both the acid hydrolysis of the N-protecting group and the subsequent formation of the napsylate salt of talampicillin.

In a further modification, ampicillin napsylate can act as the source of ampicillin and also as the source of napsylate ion. In this modification the ampicillin napsylate may be reacted with a suitable source of the phthalidyl group, such as phthalidyl bromide, suitably under neutral conditions, to yield the desired product.

In an alternative reaction sequence, phthalidyl 6-APA of formula (B):

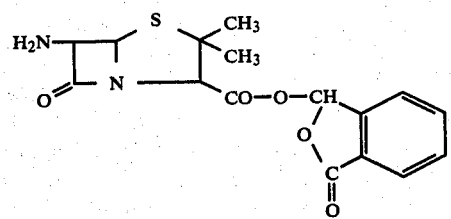

wherein the amino group is optionally substituted with a group which permits acylation to take place, is reacted with an N-acylating derivative of phenylglycine napsylate of formula (C):

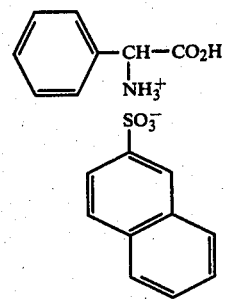

Suitably this reaction is carried out under neutral conditions.

Suitable groups which permit acylation to take place and which are optionally present on the amino group of the starting material of the formula (B) include N-silyl, N-stannyl and N-phosphorus groups, for example trialkylsilyl groups such as trimethylsilyl, trialkyltin groups such as tri-n-butyltin, groups of formula —P.R$^a$R$^b$ wherein R$^a$ is an alkyl, haloalkyl, aryl, aralkyl, alkoxy, haloalkoxy, aryloxy, aralkyloxy or dialkylamino group, R$^b$ is the same as R$^a$ or is halogen or R$^a$ and R$^b$ together form a ring; suitable such phosphorus groups being —P(OC$_2$H$_5$)$_2$, —P(C$_2$H$_5$)$_2$,

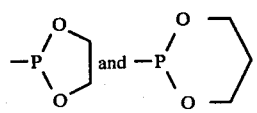

A reactive N-acylating derivative of the acid is employed in the above process.

Suitable N-acylating derivatives include an acid halide, preferably the acid chloride or bromide.

The acid halide may be prepared by reacting the acid (C) or a salt thereof with a halogenating (e.g. chlorinating or brominating) agent such as phosphorus pentachloride, thionyl chloride or oxalyl chloride.

Alternatively, the N-acylating derivative of the acid (C) may be symmetrical or a mixed anhydride. Suitable mixed anhydrides are alkoxyformic anhydrides, or anhydrides with, for example, carbonic acid monoesters.

Other reactive N-acylating derivatives of the acid (C) include the reactive intermediate formed by reaction in situ with a condensing agent such as a carbodiimide.

A further alternative reaction sequence comprises:

(a) reacting a compound of formula (D)

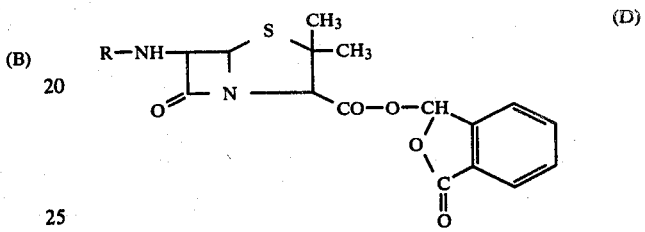

wherein the group R is an organic acyl group (preferably of a naturally-occurring penicillin), with an agent forming an imino halide on the 6-amino carbon atom;

(b) reacting the resulting compound to introduce a group QR$_f$ on the imino carbon atom, wherein Q is oxygen, sulphur or nitrogen and R$_f$ is an alkyl group of from 1 to 12 carbon atoms, or an aralkyl group of from 5 to 14 carbon atoms, to form an iminoether, iminothioether or amidine (when Q is O, S or N respectively);

(c) reacting with a reactive derivative of an acid of formula (C) above and (d) treating with water or an alcohol.

The invention also provides a pharmaceutical composition, which composition comprises talampicillin napsylate and a pharmaceutically acceptable carrier.

The invention further provides a process for the preparation of this composition, which process comprises bringing the ingredients thereof into association.

The pharmaceutical compositions of this invention may be presented in single dose, multi-dose, or fractional dose form as convenient and appropriate. Single dose compositions will suitably contain a weight of talampicillin napsylate equivalent to an effective dose of talampicillin hydrochloride, such as 10 to 500 mg. of talampicillin hydrochloride, for example 125 or 250 mg. Multi-dose and fractional dose compositions will suitably contain proportionate amounts of talampicillin napsylate.

A particularly preferred composition of the invention is a powder for reconstitution into a syrup (suspension), as it is in this presentation form that talampicillin napsylate's advantageous properties of improved taste and effective bioavailability are most well employed.

Thus the invention provides a pharmaceutical composition in the form of a powder which may be reconstituted with water to form a syrup, which powder comprises talampicillin napsylate and a syrup additive.

The powder may be prepared by simple mixing of the ingredients, for example using a planetary mixer, Y-cone blender or similar apparatus conventionally used in the preparation of penicillin syrup powders.

In this powder the talampicillin napsylate is suitably of low particle size, as of course is conventional for syrup powders.

Syrup additives are present to improve the stability, appearance and palatability of the resultant made up syrup. Examples of such additives include flavours, sugar, dyes, anti-foaming agents, thickeners, buffering agents and the like.

One particularly preferred additive for inclusion in the powder is sugar. Often sugar will represent 30 to 95% of the powder, more suitably 60 to 90% of the powder.

The powder may be presented for use for example in single dose sachets or in multi-dose bottles.

A single dose of the powder will suitably contain the weight of talampicillin napsylate equivalent to an effective dose of talampicillin hydrochloride, such as for example 125 mg. or 250 mg. of talampicillin hydrochloride. However it will be appreciated that smaller quantities of active ingredient may be used for therapy of infants. Thus while a single dose of the powder will often contain a weight of talampicillin napsylate equivalent to 125 or 250 mg. of talampicillin hydrochloride, it may also contain lesser weights such as for example weights equivalent to 31.25 or 62.5 mg. of talampicillin hydrochloride for therapy of infants or young children.

Talampicillin napsylate may also be formulated into tablets (when used herein 'tablet' includes 'dispersible tablet'). Thus in a further aspect, the invention provides a tablet, which tablet comprises talampicillin napsylate.

Such tablets will also of course comprise one or more tablet additives. Suitable examples of such additives include diluents, disintegrants, lubricants, binders and the like, and in addition for dispersible tablets, flavours, sweeteners and buffering agents and the like. Normally such tablets will comprise 15 to 80% talampicillin napsylate and 20 to 85% additives, more suitably 20 to 60% and 40 to 80% respectively.

The tablets of the invention may be prepared in conventional manner, for example by direct compression.

Usually the tablets of the invention will weigh 100 to 2500 mg., suitably 100 to 2000 mg., more suitably 300 to 1700 mg. Normally dispersible tablets will have a weight toward the higher end of these weight ranges.

Talampicillin napsylate may also be formulated into capsules. Such capsules will suitably of course also contain conventional additives such as diluents, disintegrants, lubricants and the like. In such capsules the talampicillin napsylate will suitably represent 40 to 99% of the capsule contents.

The capsules may be prepared in normal manner, for example by filling the mixed ingredients into empty capsule shells.

Suitably the tablets and capsules of the invention will contain the weight of talampicillin napsylate equivalent to an effective dose of talampicillin hydrochloride. Thus they will often contain a weight of talampicillin napsylate equivalent to 125 or 250 mg. of talampicillin hydrochloride. It will be appreciated however that the tablets and capsules could quite easily contain fractional doses of active ingredient, but then of course two or more such tablets or capsules would have to be taken at one time to yield the desired effective dose.

Talampicillin napsylate, and syrups, tablets and capsules prepared therefrom as hereinbefore described, have useful stability.

The invention also provides a method of treatment of infection, which method comprises administering to the sufferer an effective amount of talampicillin napsylate.

Normally of course the talampicillin napsylate will be administered in the form of a composition of the invention, and so in this case sufficient of the chosen composition must be administered to give the effective amount of talampicillin napsylate.

The 'effective amount' of talampicillin napsylate will be, as hereinbefore discussed, the weight thereof equivalent to an effective dose of talampicillin hydrochloride. This effective dose of talampicillin hydrochloride will, as hereinbefore discussed, normally be 125 or 250 mg., but as pointed out (especially with syrups) lesser amounts may be used with infants and young children.

The administration will normally be repeated, for example following the dosage regime conventionally used for talampicillin hydrochloride.

The following Examples illustrate the invention.

EXAMPLES 1 TO 7

These Examples illustrate the preparation of talampicillin napsylate.

EXAMPLE 1

Sodium naphthalene-2-sulphonate 12.5 g. (0.054 moles) was dissolved in water (300 ml) at 35°–40°, filtered and cooled to 20°. This was added with stirring to a solution of talampicillin HCL (25 g. activity weight, 0.048 moles) in water (500 ml) at 22°–25° over 15 minutes.

The solution was cooled to ca 5°–10° and the product isolated by filtration, reslurried in water (250 ml) for 30 minutes and the product isolated and dried in a fluid bed dryer at 20°–25° initially, then increasing the temperature gradually to 50°. Yield 30 g. of talampicillin napsylate.

EXAMPLE 2

Identical to Example 1 except that naphthalene sulphonic acid (12.5 g.) was used.

EXAMPLE 3

Identical to Example 1 except that the sodium-2-naphthalene sulphonate solution was acidified with concentrated hydrochloric acid (5.0 ml.) before addition to the talampicillin solution.

In Examples 1 to 3 the order of addition can be reversed if desired.

EXAMPLE 4

Sodium naphthalene-2-sulphonate (150 g.) was dissolved in water (4 liters) at 35°–40°, filtered, cooled to 20° and acidified with concentrated hydrochloric acid (60 ml.).

This was added with stirring to a solution of talampicillin HCL (300 g. activity weight) in water (6.5 liters) at 22°–25° over 15 minutes then cooled to 5°–10°.

Precipitated product was isolated, reslurried in water (3.5 liters) re-isolated, dissolved in methylene dichloride (3.0 liters), separated from water and desiccated over molecular sieve (200 g. type 4A). The filtered solution was spray dried to give 320 g. of talampicillin napsylate.

EXAMPLE 5

Sodium naphthalene-2-sulphonate (150 g.) and water (6.0 liters) were stirred for ca 15 minutes at 20°–25°. Hydrochloric acid (60 ml.), methylene dichloride (3.5 liters) and talampicillin HCL (300 g. activity weight) were then added, and stirring was continued for 15 minutes.

The talampicillin napsylate produced was located entirely in the organic phase. After washing with water (4×5.0 liters) this was desiccated over molecular sieve prior to spray drying to give 350 g. of talampicillin napsylate.

EXAMPLE 6

A solution of sodium naphthalene-2-sulphonate was prepared by adding sodium naphthalene-2-sulphonate (12.5 g.) to a stirred solution of PVP (12.5 g.) in water (125 ml) at 35°–40° C. After dissolution the solution was filtered, acidified with concentrated hydrochloric acid (5.0 ml.) and cooled to 20°–25° C.

Talampicillin hydrochloride (25 g.) was added to a stirred solution of PVP (25 g.) in water (250 ml.) at 20°–25° C. When dissolved the solution was filtered into the precipitation vessel.

The temperature was adjusted to 25°–27° C. and the sodium naphthalene-2-sulphonate solution was added with stirring over ca 30 minutes. The slurry was cooled to 5°–10° C. and filtered. The product was reslurried in water (250 ml.) and dried in a fluid bed drier to give 30 g. of talampicillin napsylate.[PVP m.wt:10,000].

EXAMPLE 7

1. Preparation of Sodium-[D-N-(1-methoxycarbonylpropen-2-yl)α-aminophenyl-acetamido]-penicillinate A slurry of 6-aminopenicillanic acid (77 g.) in a mixture of water (85 ml.) and acetone (125 ml.) at 0°–5° C. was treated with 15% potassium hydroxide solution to give a clear solution at pH 9.0, then cooled to −22° C.

At the same time a mixed anhydride was prepared by adding sodium D-N-(1-methoxycarbonyl-propen-2-yl)α-aminophenyl acetate (100.5 g.) to a mixture of ethylchloroformate (37.4 ml.) and dimethylaminopropanol (1.22 ml.) in acetone (300 ml.) at −50° C. After ca 20 minutes this was added to the 6-aminopenicillanic acid solution, and stirring was continued for 20 minutes.

2. Esterification of Product from (1)

To the reaction product solution were added water (250 ml.), sodium bicarbonte (70 g.), tributylethylammonium ethosulphate (48 ml of 80% aqueous solution) and bromophthalide (100 g.) in methylene dichloride (400 ml.).

The temperature was raised to 28°–29° C., stirring was continued for 1.5 hours and water (650 ml.) was added.

The lower methylene dichloride phase containing the required phthalidyl ester of (1) was isolated and washed with water (1350 ml., 1500 ml.).

3. Hydrolysis of Product from (2)

To the methylene dichloride solution was added water (1100 ml.) and concentrated hydrochloric acid (54 ml. of 31% w/w). The mixture was stirred for 15 minutes at 20° C. Heptane (400 ml) was added and stirring was continued for 45 minutes.

The lower aqueous layer containing talampicillin was isolated, diluted with water (385 ml.) and warmed to 30° C. The solution was washed with heptane (2×770 ml.).

4. Precipitation of Talampicillin Napsylate

A solution of sodium naphthalene sulphonate (77 g.) in water (1540 ml.) was prepared at 35°–40° C., filtered, acidified with concentrated hydrochloric acid (30 ml.) and cooled to 20° C.

To this solution was added the talampicillin solution from (3) over ca 30 minutes, maintaining the temperature at 20°–22° C. The slurry was cooled to 5°–10° C., filtered and washed with cold water (2 liters). The product was dried in a fluid bed drier to give 185 g. of talampicillin napsylate.

EXAMPLE 8

The N-(1-methoxy carbonyl propen-2-yl) of talampicillin (20 g.) was dissolved in methylene dichloride (100 ml). Naphthalene-2-sulphonic acid (10 g) dissolved in water (100 mls.) was added, and the mixture was stirred for one hour at 5° to 10° C. The organic phase was separated, and added dropwise to isopropyl ether (450 mls.), to precipitate the talampicillin napsylate (20 g.).

EXAMPLE 9

This Example illustrates the preparation of powder containing talampicillin napsylate, for reconstitution into syrups.

The following formulations were prepared by mixing together the stated ingredients in the appropriate proportions in a Y-cone blender, and then filling the stated weight of powder into the unidose sachet and 20 ml., 60 ml., 75 ml., and 100 ml., bottles.

The talampicillin napsylate was used after sieving with a 750 μm (20 mesh) sieve.

| Ingredients | Unidose Sachet mg. | 20 ml. bottle g. | 60 ml. bottle g. | 75 ml. bottle g. | 100 ml. bottle g. | % w/w |
|---|---|---|---|---|---|---|
| Disodium Edetate | 2.834 | 0.012 | 0.036 | 0.045 | 0.060 | 0.0800 |
| Sodium Benzoate | 4.723 | 0.020 | 0.060 | 0.075 | 0.100 | 0.1333 |
| Sodium methyl hydroxybenzoate | 2.834 | 0.012 | 0.036 | 0.045 | 0.060 | 0.0800 |
| Xanthan gum | 7.795 | 0.033 | 0.099 | 0.124 | 0.165 | 0.2200 |
| Anti-foam agent | 3.780 | 0.016 | 0.048 | 0.060 | 0.080 | 0.1067 |
| Erythrosine | 0.567 | 0.002 | 0.007 | 0.009 | 0.012 | 0.0160 |
| Flavours | 136.858 | 0.579 | 1.738 | 2.174 | 2.897 | 3.8627 |
| Talampicillin napsylate (pure basis) | 176.445 | 0.747 | 2.241 | 2.801 | 3.735 | 4.9800 |
| Sucrose to | 3543.072 | 15.000 | 45.000 | 56.250 | 75.000 | 100.0000 |

These formulations provided a nominal 167 mg. talampicillin napsylate per dose, equivalent to 125 mg. talampicillin hydrochloride per dose, and also provided the usual overage of approximately 10%.

Corresponding formulations providing an equivalent of 250 mg. talampicillin hydrochloride per dose can be made in analogous manner.

EXAMPLE 10

This Example illustrates the preparation of talampicillin napsylate syrups.

Syrups were prepared from the formulations of Example 9 by adding thereto 15 ml (unidose sachet), 11 ml. (20 ml. bottle), 32 ml. (60 ml. bottle), 40 ml. (75 ml. bottle) and 55 ml. (100 ml. bottle of purified water, to give approximately 17 ml., 20 ml., 60 ml., 80 ml., and 100 ml., of syrup respectively.

EXAMPLE 11

Bioavailability

In a blood level study in volunteers, similar biological availability of ampicillin was demonstrated after oral administration of equivalent dosages of talampicillin hydrochloride in tablet form and talampicillin napsylate in syrup form.

EXAMPLE 12

Stability (a) Our stability tests have demonstrated that powders prepared as in Example 9 have a shelf life of at least 18 months at 20° C.

(b) Similarly, stability tests on reconstituted syrups of four different strengths (talampicillin napsylate equivalent to 250 mg., 125 mg., 62.5 mg., and 31.25 mg., of talampicillin hydrochloride in 5 ml. of water) have shown these syrups to have a shelf life of at least 7 days in a cool place.

What we claim is:

1. Ampicillin phthalidyl ester naphthalene 2-sulphonate of the formula (A):

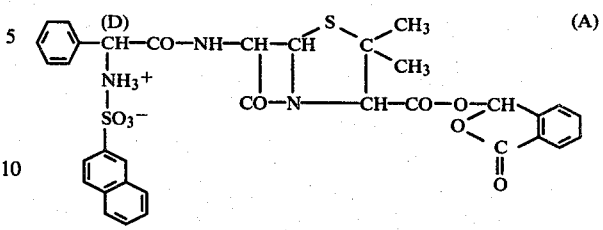

2. A pharmaceutical composition of improved taste and palatability having the anti-infective activity of ampicillin, which upon ingestion provides biological availability of ampicillin, which composition comprises an effective amount of ampicillin phthalidyl ester naphthalene-2-sulphonate sufficient to produce a high serum concentration of ampicillin and a pharmaceutically acceptable carrier.

3. A composition according to claim 2, in the form of a powder which may be reconstituted with water to form a syrup, which powder comprises ampicillin phthalidyl ester naphthalene-2-sulphonate, and a syrup additive.

4. A composition according to claim 3, wherein the powder contains sugar.

5. A composition according to claim 2, containing a weight of ampicillin phthalidyl ester naphthalene-2-sulphonate equivalent to 250 mg. of talampicillin hydrochloride.

6. A composition according to claim 2, containing a weight of ampicillin phthalidyl ester naphthalene-2-sulphonate equivalent to 125 mg. of talampicillin hydrochloride.

7. A composition according to claim 2 in unit, fractional unit or multi-unit dosage form.

8. A composition according to claim 7 in which the dosage form is a tablet or capsule.

* * * * *